US012636616B2

(12) United States Patent
Wang et al.

(10) Patent No.: US 12,636,616 B2
(45) Date of Patent: May 26, 2026

(54) PAPER-BASED MICRO-CONCENTRATOR, BIOLOGICAL SAMPLE DETECTION DEVICE AND BIOLOGICAL SAMPLE DETECTION METHOD

(71) Applicant: National Chung Cheng University, Chiayi (TW)

(72) Inventors: Shau-Chun Wang, ChiaYi City (TW); Lai-Kwan Chau, Chiayi City (TW); Jia-Jie Lin, Taichung City (TW); Yuan-Yu Chen, Nantou City (TW); Ya-Chuan Chen, Taipei City (TW)

(73) Assignee: National Chung Cheng University, Chiayi (TW)

( * ) Notice: Subject to any disclaimer, the term of this patent is extended or adjusted under 35 U.S.C. 154(b) by 981 days.

(21) Appl. No.: 17/813,428

(22) Filed: Jul. 19, 2022

(65) Prior Publication Data

US 2023/0338898 A1     Oct. 26, 2023

(30) Foreign Application Priority Data

Apr. 22, 2022    (TW) .................................. 111115505

(51) Int. Cl.
| | |
|---|---|
| *B01D 61/48* | (2006.01) |
| *C12Q 1/6837* | (2018.01) |
| *G01N 1/40* | (2006.01) |
| *G01N 27/447* | (2006.01) |

(52) U.S. Cl.
CPC ........... *B01D 61/48* (2013.01); *C12Q 1/6837* (2013.01); *G01N 1/4005* (2013.01); *G01N 27/44791* (2013.01); *B01D 2311/2623* (2013.01); *G01N 2001/4011* (2013.01)

(58) Field of Classification Search
CPC .... B01D 61/48; B01D 63/005; B01D 63/028; B01D 63/088; B01D 2311/2623; C12Q 1/6837; G01N 27/447; G01N 1/4005; G01N 27/44791; G01N 2001/4011; G01N 27/44765; G01N 30/90; G01N 1/405; G01N 2001/4016; G01N 30/74; B01L 3/50273; B01L 3/502715; B01L 3/502761; B01L 3/502707; B01L 2300/0627; B01L 2400/088; B01L 2200/12; B01L 2300/126;
(Continued)

(56) References Cited

U.S. PATENT DOCUMENTS

2010/0187112 A1* 7/2010 Han ..................... B01L 3/50273
                                                    204/451
2015/0093304 A1* 4/2015 Guzman .......... G01N 27/44743
                                                    422/527
2017/0136457 A1* 5/2017 Bercovici ........... B01L 3/50273

* cited by examiner

*Primary Examiner* — Xiuyu Tai

(57) ABSTRACT

A paper-based micro-concentrator includes a bearing substrate, a fluid reservoir unit, a filter paper, an external electric field, an ion exchange membrane and a magnet. The fluid reservoir unit includes a first buffer solution tank and a second buffer solution tank, which are interval disposed on the bearing substrate. The filter paper is disposed on the bearing substrate, and two ends of the filter paper are respectively placed in the first buffer solution tank and the second buffer solution tank. The external electric field includes a cathode and an anode, which are respectively placed in the first buffer solution tank and the second buffer solution tank. The ion exchange membrane is disposed on the filter paper and close to the first buffer solution tank. The magnet is movably disposed under the bearing substrate.

13 Claims, 14 Drawing Sheets
(3 of 14 Drawing Sheet(s) Filed in Color)

Specification includes a Sequence Listing.

(58) Field of Classification Search
CPC ....... B01L 2300/161; B01L 2400/0421; B01L 2300/165; B01L 2300/04
See application file for complete search history.

400

410 A biological sample detection device is provided

420 A sample mixing step is performed

430 A sample adding step is performed

440 A concentrating step is performed

450 A detecting step is performed

PAPER-BASED MICRO-CONCENTRATOR, BIOLOGICAL SAMPLE DETECTION DEVICE AND BIOLOGICAL SAMPLE DETECTION METHOD

RELATED APPLICATIONS

This application claims priority to Taiwan Application Serial Number 111115505, filed Apr. 22, 2022, which is herein incorporated by reference.

SEQUENCE LISTING

The sequence listing submitted via EFS, in compliance with 37 CFR § 1.52(e)(5), is incorporated herein by reference. The sequence listing XML file submitted via EFS contains the file "CP-5442-US_SEQ_LIST", created on Jul. 13, 2022, which is 3,530 bytes in size.

BACKGROUND

Technical Field

The present disclosure relates to a micro-concentrator, a biological sample detection device and a biological sample detection method. More particularly, the present disclosure relates to a paper-based micro-concentrator, a biological sample detection device including the paper-based micro-concentrator, and a biological sample detection method using the same.

Description of Related Art

Microfluidic systems have the characteristics of reducing sample and reagent consumption, rapid detection, and easy portability. In recent years, the rapid development of microfluidic systems has become an emerging field that scientists are eager to study. With the advancement of micro-electro mechanical system (MEMS) technology, the functions of microfluidic chips are becoming more and more diverse. Steps including sample injection, mixing, concentration, detection, etc., can all be implemented in the same microfluidic chip that has been precisely designed, which can be called Lab on a chip. Furthermore, the microfluidic system combined with biosensing technology is suitable as an ideal detection platform.

Compared with conventional microfluidic systems using silica or polymer substrates, a paper-based microfluidic system has many advantages such as low cost, simple fabrication process, easier operation, relatively low environmental pollution, and good portability. In addition, the paper-based microfluidic system is suitable for areas where resources are relatively scarce and can be easily applied to on-site testing and real-time detection. The paper-based microfluidic system combined with the analysis and detection technology can be used as a simple detection device. The experimental process of the paper-based microfluidic system is relatively simple, steps including injection and concentration of samples and detection can be performed in the same paper strip, which can reduce sample loss, so that the paper-based microfluidic systems is worthy of study.

Biological samples are generally very low in concentration and very limited in amount, so it is important to improve the detection limit and detection sensitivity of a detection device. In addition, in order to avoid cross-contamination caused by secondary use, a low-cost, disposable, massproduced micro-concentrator with high detection sensitivity has the potential to be developed.

SUMMARY

According to one aspect of the present disclosure, a paper-based micro-concentrator is provided. The paper-based micro-concentrator includes a bearing substrate, a fluid reservoir unit, a filter paper, an external electric field, an ion exchange membrane and a magnet. The fluid reservoir unit includes a first buffer solution tank and a second buffer solution tank, wherein the first buffer solution tank and the second buffer solution tank are interval disposed on the bearing substrate, and the first buffer solution tank and the second buffer solution tank store a buffer solution, respectively. The filter paper is disposed on the bearing substrate, and two ends of the filter paper are respectively placed in the first buffer solution tank and the second buffer solution tank. The external electric field includes a cathode and an anode, and the cathode and the anode are respectively placed in the first buffer solution tank and the second buffer solution tank. The ion exchange membrane is disposed on the filter paper and close to the first buffer solution tank. The magnet is movably disposed under the bearing substrate.

According to another aspect of the present disclosure, a biological sample detection device for detecting an analyte in a biological sample is provided. The biological sample detection device includes the paper-based micro-concentrator according to the aforementioned aspect and a probe set. The probe set includes a detection probe and a capture probe. The detection probe includes a label and a first identifying element, and the capture probe includes a magnetic nanoparticle and a second identifying element. The first identifying element and the second identifying element are different, and the first identifying element and the second identifying element specifically bind to the analyte, respectively.

According to still another aspect of the present disclosure, a biological sample detection method includes steps as follows. The biological sample detection device according to the aforementioned aspect is provided. A sample mixing step is performed, wherein the probe set is mixed with a biological sample, and the detection probe and the capture probe in the probe set are respectively bound to an analyte in the biological sample to form a complex. A sample adding step is performed, wherein the biological sample including the complex is dropped onto the filter paper of the paper-based micro-concentrator. A concentrating step is performed, wherein a voltage is applied to the paper-based micro-concentrator for a concentration time to form a concentrating area. A detecting step is performed, wherein the concentrating area is detected with a detection instrument to detect a concentration of the analyte.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

The present disclosure will be further exemplified by the following embodiments. However, the embodiments can be embodied in various specific ranges. The specific embodiments are only for the purposes of description and are not limited to these practical details thereof.

I. A PAPER-BASED MICRO-CONCENTRATOR
OF THE PRESENT DISCLOSURE

A paper-based micro-concentrator of the present disclosure includes a bearing substrate, a fluid reservoir unit, a filter paper, an external electric field, an ion exchange membrane and a magnet. The fluid reservoir unit includes a first buffer solution tank and a second buffer solution tank, wherein the first buffer solution tank and the second buffer solution tank are interval disposed on the bearing substrate, and the first buffer solution tank and the second buffer solution tank store a buffer solution respectively. The filter paper is disposed on the bearing substrate, and two ends of the filter paper are respectively placed in the first buffer solution tank and the second buffer solution tank. The external electric field includes a cathode and an anode, and the cathode and the anode are respectively placed in the first buffer solution tank and the second buffer solution tank. The ion exchange membrane is disposed on the filter paper and close to the first buffer solution tank. The magnet is movably disposed under the bearing substrate. The ion exchange membrane can be a cation exchange membrane or an anion exchange membrane. When the ion exchange membrane is the cation exchange membrane, a surface of the filter paper can have a negatively charged functional group, the cathode is placed in the first buffer solution tank, and the anode is placed in the second buffer solution tank. When the ion exchange membrane is the anion exchange membrane, the surface of the filter paper can have a positively charged functional group, the anode is placed in the first buffer solution tank, and the cathode is placed in the second buffer solution tank.

Figure 1:
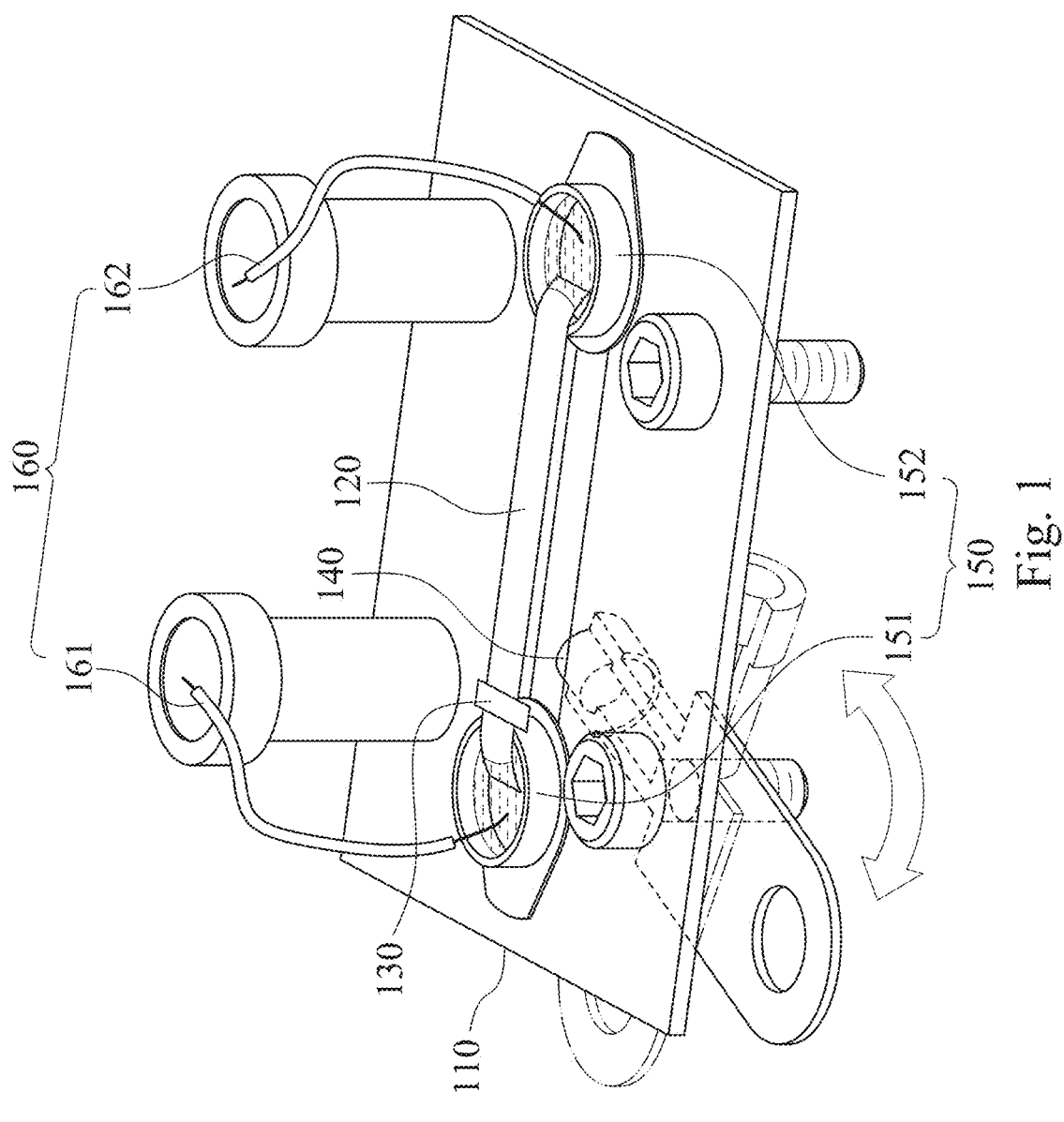
FIG. 1 is a schematic view of a paper-based micro-concentrator according to one example of one embodiment of the present disclosure.

Please refer to FIG. 1, which is a schematic view of a paper-based micro-concentrator 100 according to one example of one embodiment of the present disclosure, wherein the ion exchange membrane in the paper-based micro-concentrator 100 shown in FIG. 1 is a cation exchange membrane 130 for concentrating an analyte with negative charge. The paper-based micro-concentrator 100 includes a bearing substrate 110, a fluid reservoir unit 150, a filter paper 120, an external electric field 160, the cation exchange membrane 130 and a magnet 140.

In FIG. 1, the paper-based micro-concentrator 100 includes the bearing substrate 110. The bearing substrate 110 can be made of a processed acrylic plate, and an acrylic plate with a length of 55 mm, a width of 50 mm, and a height of 3 mm is engraved by a $CO_2$ laser engraving machine as the bearing substrate 110, but the present disclosure is not limited thereto. The fluid reservoir unit 150 includes a first buffer solution tank 151 and a second buffer solution tank 152. The first buffer solution tank 151 and the second buffer solution tank 152 are interval disposed on the bearing substrate 110, for example, are fixed on the bearing substrate 110 with hot melt adhesive. The first buffer solution tank 151 and the second buffer solution tank 152 store a buffer solution respectively, wherein the description of "first" and "second" does not refer to a specific order, but is used to clearly illustrate the corresponding positional relationship between the external electric field 160 and the cation exchange membrane 130 to be set subsequently.

The filter paper 120 is disposed on the bearing substrate 110, one end of the filter paper 120 is placed in the first buffer solution tank 151, and the other end of the filter paper is placed in the second buffer solution tank 152. The filter paper 120 has the advantages of easy acquisition, low price, simple manufacture and low environmental pollution. A surface of the filter paper 120 in the paper-based micro-concentrator 100 shown in FIG. 1 has the negatively charged functional group, so it can generate an electroosmotic flow. The filter paper 120 can be made of polyvinylidene difluoride (PVDF), nitrocellulose or cellulose acetate, etc., but the present disclosure is not limited thereto. As long as the surface of the filter paper 120 has the negatively charged functional group, it can be used as the filter paper 120 in the present disclosure, and can be selected and used for different subsequent detection devices. For example, when a Raman spectrometer is used for detection, polyvinylidene chloride, which has no Raman signal, can be selected. Thus, the background interference in detection using the Raman spectrometer can be avoided when the label in the detection probe of the biological sample detection device is a Raman label. In addition, a minimum dimension of a length, a width and a height of the filter paper 120 can be greater than 0 mm and less than or equal to 1 mm. For example, the filter paper 120 can be cut to a length of 35 mm, a width of 3 mm, and a height of 1 mm, and then the two ends of the filter paper 120 are placed in the first buffer solution tank 151 and the second buffer solution tank 152 respectively, so that the buffer solution completely wets the filter paper 120 by capillary force of the filter paper 120.

The external electric field 160 includes a cathode 161 and an anode 162. The cathode 161 and the anode 162 can be platinum electrodes, but the present disclosure is not limited thereto. The cathode 161 is placed in the first buffer solution tank 151 and the anode 162 is placed in the second buffer solution tank 152 to apply an electric field to the paper-based micro-concentrator 100.

The cation exchange membrane 130 is disposed on the filter paper 120 and close to the first buffer solution tank 151, and the cation exchange membrane 130 is attached to the filter paper 120. The size of the cation exchange membrane 130 can be 6 mm in length and 3 mm in width. The material of the cation exchange membrane 130 can be polyester fiber (PES) as the base material and polyethylene (PE) as the basic adhesive, and with sulfonate ($SO_3^-$) as the negatively charged functional group, but the present disclosure is not limited thereto.

The magnet 140 is movably disposed under the bearing substrate 110, whereby the magnet 140 can be rotated into a place under the paper-based micro-concentrator 100 or rotated out of the paper-based micro-concentrator 100 according to the requirements of the experiment.

Figure 2A:
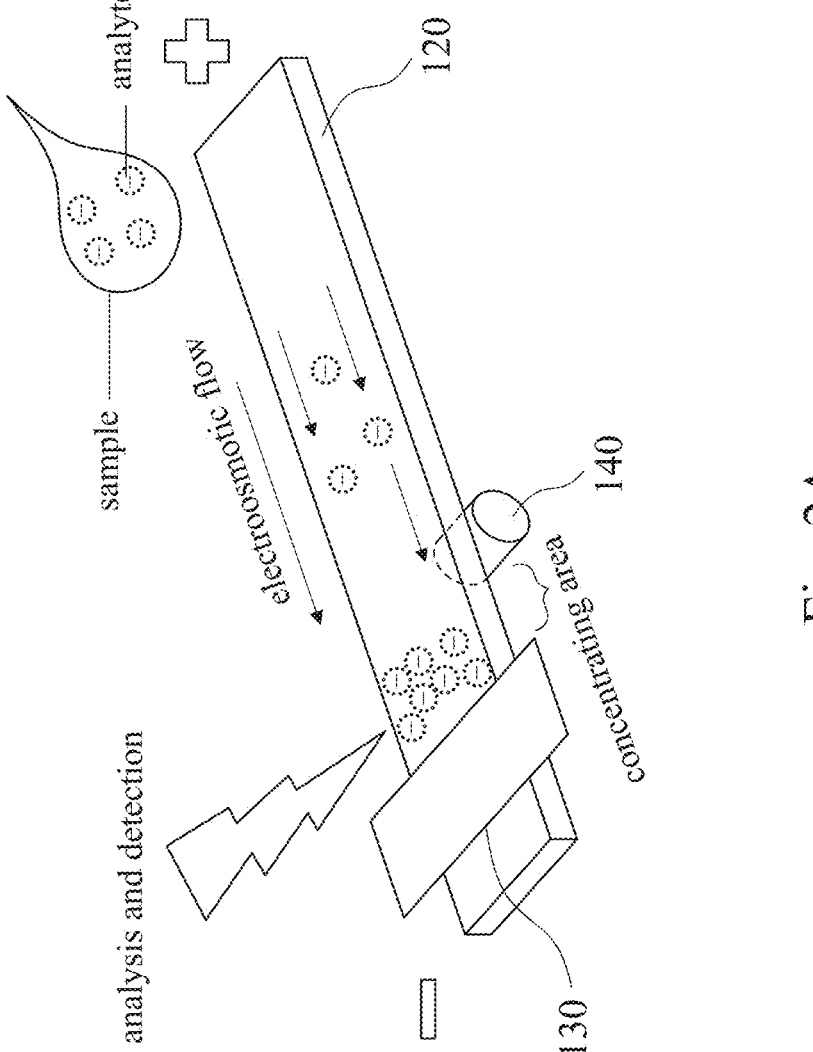
FIG. 2A is a schematic view showing an action mechanism of the paper-based micro-concentrator shown in FIG. 1.

Please refer to FIG. 2A, which is a schematic view showing an action mechanism of the paper-based micro-concentrator 100 shown in FIG. 1. The paper-based micro-concentrator 100 of the present disclosure uses the filter paper 120 as the base material of the micro-concentrator. The filter paper 120 is cut into appropriate size paper strips and wetted with an electrolyte solution. The cation exchange membrane 130 is placed on the end of the filter paper 120 close to the cathode 161 so that the cation exchange membrane 130 is attached to the filter paper 120. An electric field is applied to the paper-based micro-concentrator 100, so that the freely moving cations in a diffuse layer of an electric double layer on the surface of the filter paper 120 move towards an electrode with opposite charge, and overall solution is driven to flow from the anode 162 to the cathode 161 to generate the electroosmotic flow. However, the cation exchange membrane 130 is attached on the end of the filter paper 120 close to the cathode 161, and the cation exchange membrane 130 only allows cations to pass through the pores, resulting in a large number of cations accumulating in the cation exchange membrane 130 close to the cathode 161, forming an ion enrichment zone. When a large number of cations pass through the pores of the cation exchange membrane 130, a cation depletion occurs in the area of the cation exchange membrane 130 close to the anode 162, resulting in the formation of an ion depletion zone. The ion depletion zone can be used to concentrate the analyte with negative charge in the sample. When the electric field is continuously applied to the paper-based micro-concentrator 100, an ion concentration polarization will occur, and the generated electroosmotic flow will continuously drive the analyte to the edge of the ion depletion zone. The accumulation of a plurality of the analytes with negative charge at the edge of the ion depletion zone results in concentration, which eventually forms a concentrating area.

Figure 2B:
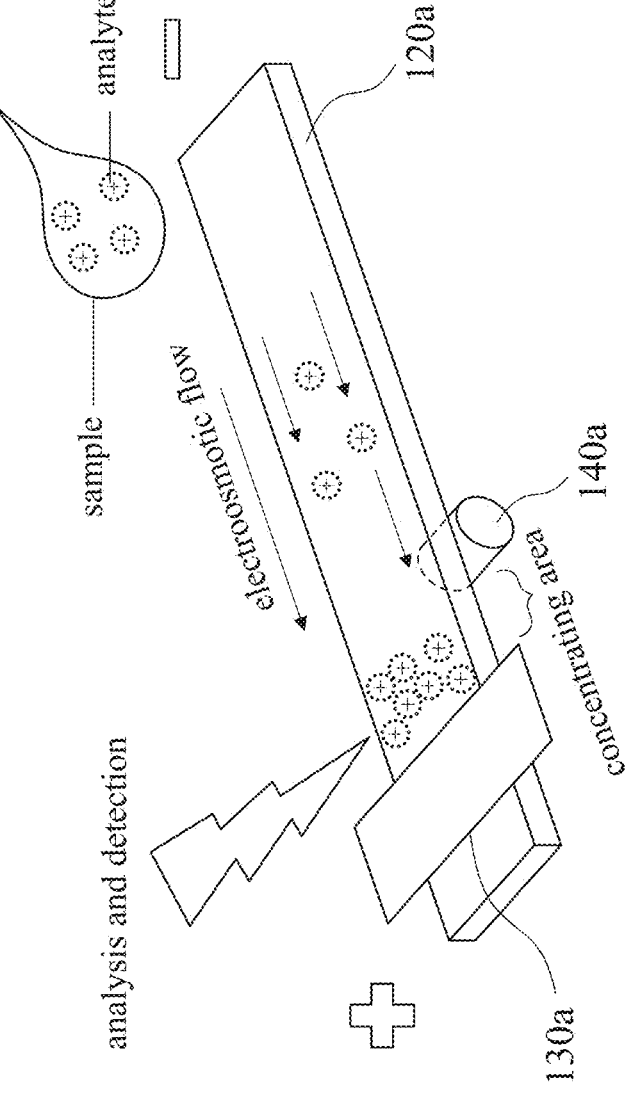
FIG. 2B is a schematic view showing an action mechanism of a paper-based micro-concentrator according to another example of one embodiment of the present disclosure.

Please refer to FIG. 2B, which is a schematic view showing an action mechanism of a paper-based micro-concentrator 100a according to another example of one embodiment of the present disclosure. The paper-based micro-concentrator 100a includes a bearing substrate (not shown), a fluid reservoir unit (not shown), a filter paper 120a, an external electric field (not shown), an anion exchange membrane 130 and a magnet 140a. The structure of the paper-based micro-concentrator 100a is similar to that of the paper-based micro-concentrator 100 shown in FIG. 1, but the ion exchange membrane in the paper-based micro-concentrator 100a is an anion exchange membrane 130a for concentrating an analyte with positive charge, and a surface of the filter paper 120a has the positively charged functional group.

The paper-based micro-concentrator 100a of the present disclosure uses the filter paper 120a as the base material of the micro-concentrator. The filter paper 120a is cut into appropriate size paper strips and wetted with the electrolyte solution. The anion exchange membrane 130a is placed on the end of the filter paper 120a close to an anode (represented by "+" in FIG. 2B) so that the anion exchange membrane 130a is attached to the filter paper 120a. The electric field is applied to the paper-based micro-concentrator 100a, so that the freely moving cations in the diffuse layer of the electrical double layer on the surface of the filter paper 120a move towards the electrode with opposite charge, and overall solution is driven to flow from a cathode (represented by "−" in FIG. 2B) to the anode to generate the electroosmotic flow. However, the anion exchange membrane 130a is attached on the end of the filter paper 120a close to the anode, and the anion exchange membrane 130a only allows anions to pass through the pores, resulting in a large number of anions accumulating in the anion exchange membrane 130a close to the anode, forming the ion enrichment zone. When a large number of anions pass through the pores of the anion exchange membrane 130a, an anion depletion occurs in the area of the anion exchange membrane 130a close to the cathode, resulting in the formation of the ion depletion zone. The ion depletion zone can be used to concentrate the analyte with positive charge in the sample. When the electric field is continuously applied to the paper-based micro-concentrator 100a, the ion concentration polarization will occur, and the generated electroosmotic flow will continuously drive the analyte to the edge of the ion depletion zone. The accumulation of a plurality of the analytes with positive charge at the edge of the ion depletion zone results in concentration, which eventually forms the concentrating area.

Figure 3:
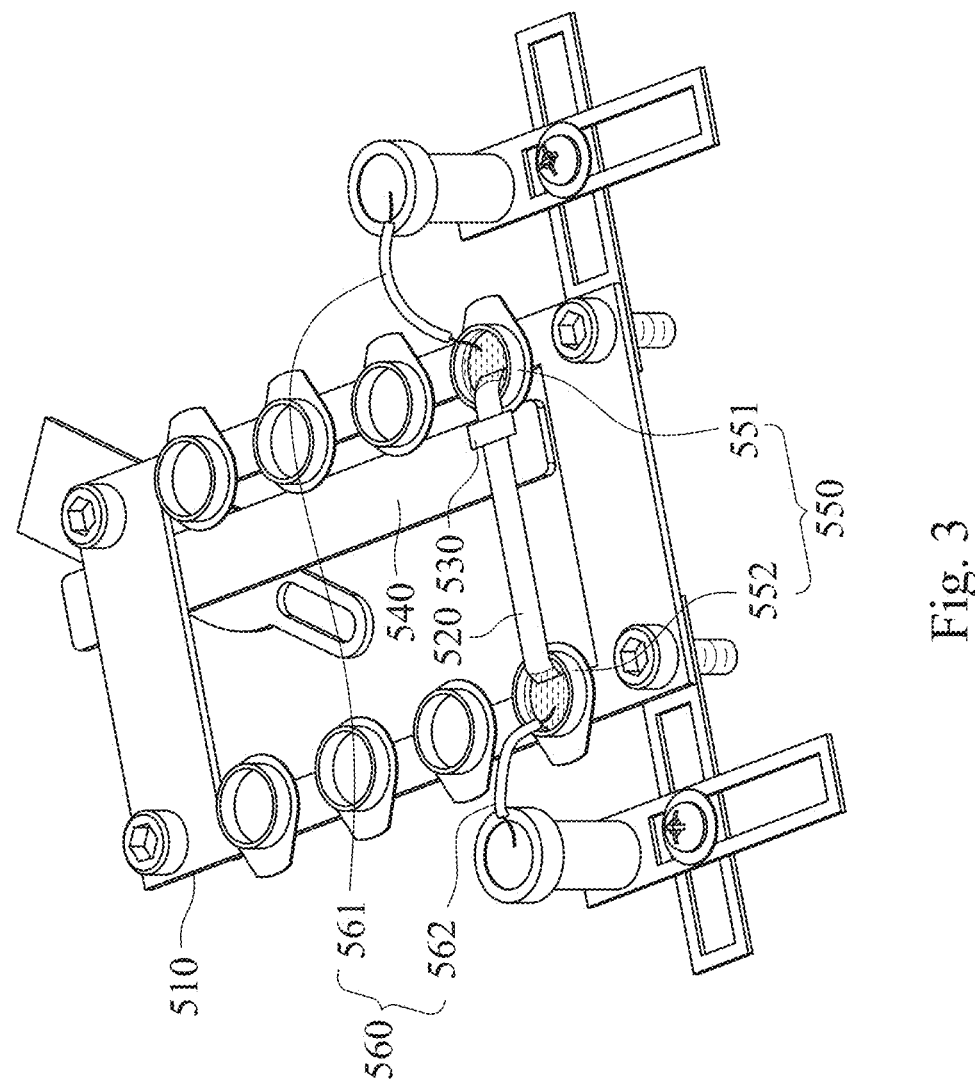
FIG. 3 is a schematic view of a paper-based micro-concentrator according to still another example of one embodiment of the present disclosure.
Figure 4:
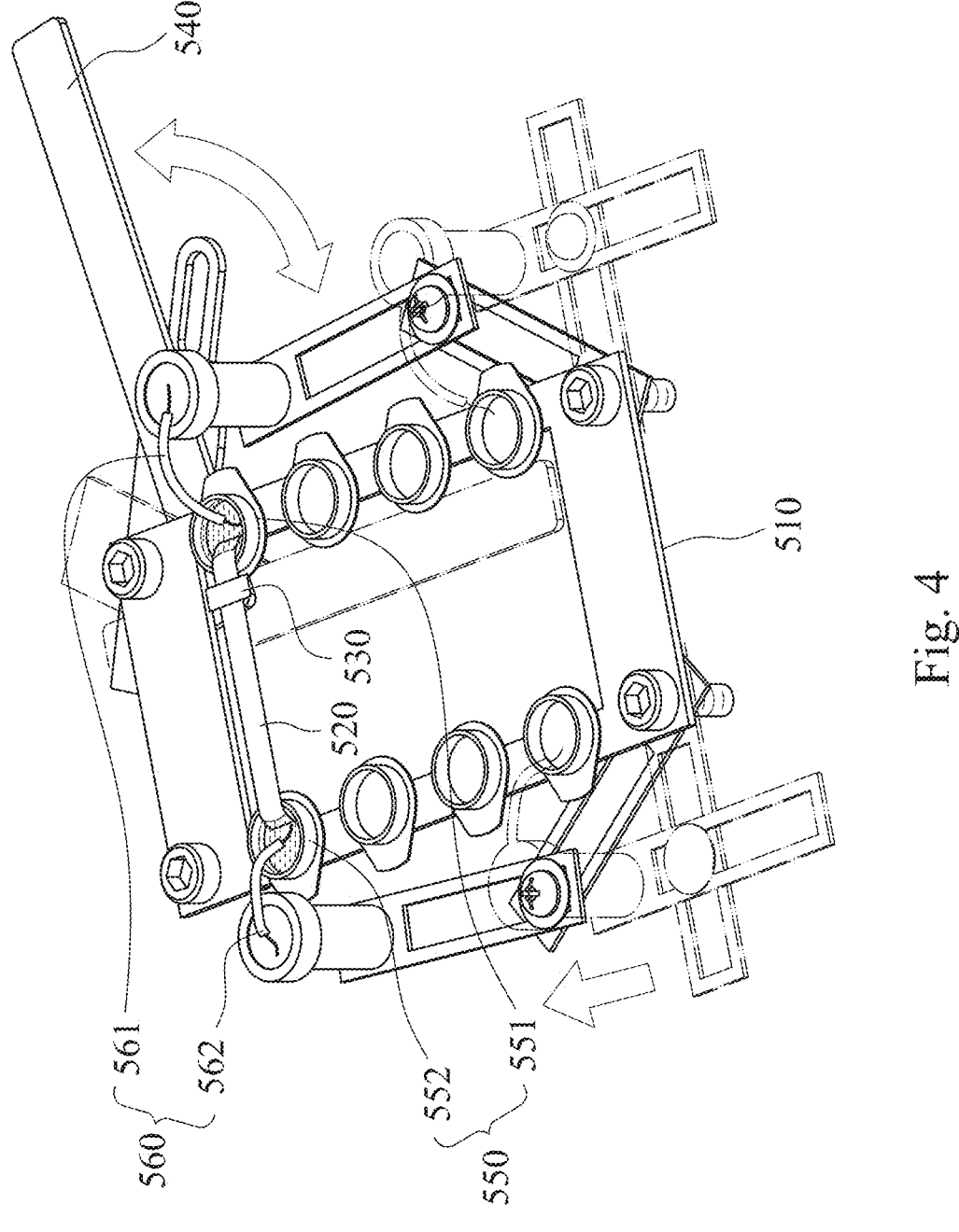
FIG. 4 is a schematic view showing an operation of the paper-based micro-concentrator shown in FIG. 3.

Please refer to FIG. 3 and FIG. 4. FIG. 3 is a schematic view of a paper-based micro-concentrator 500 according to still another example of one embodiment of the present disclosure. FIG. 4 is a schematic view showing an operation of the paper-based micro-concentrator 500 shown in FIG. 3. The paper-based micro-concentrator 500 includes a bearing substrate 510, a plurality of fluid reservoir units 550, a plurality of filter papers 520, an external electric field 560, a plurality of cation exchange membranes 530 and a magnet 540, wherein a number of the fluid reservoir units 550, a number of the filter papers 520 and a number of the cation exchange membranes 530 are the same.

In FIG. 3, the structure of the paper-based micro-concentrator 500 is similar to that of the paper-based micro-concentrator 100, but the number of the fluid reservoir units 550, the number of filter papers 520 and the number of cation exchange membranes 530 are increased, so that the paper-based micro-concentrator 500 can perform multi-concentration and repeatable experiments.

The paper-based micro-concentrator 500 includes the bearing substrate 510. The bearing substrate 510 can be made of the processed acrylic plate, and the acrylic plate with a length of 100 mm, a width of 55 mm, and a height of 3 mm is engraved by the $CO_2$ laser engraving machine as the bearing substrate 510, but the present disclosure is not limited thereto.

The number of the fluid reservoir units 550 in the paper-based micro-concentrator 500 shown in FIG. 3 is 4, and the fluid reservoir units 550 are disposed on the bearing substrate 510 at equal intervals, but the present disclosure is not limited thereto. Each of the fluid reservoir units 550 includes a first buffer solution tank 551 and a second buffer solution tank 552. The first buffer solution tank 551 and the second buffer solution tank 552 are interval disposed on the bearing substrate 510, for example, are fixed on the bearing substrate 510 with hot melt adhesive. The first buffer solution tank 551 and the second buffer solution tank 552 store the buffer solution respectively.

The external electric field 560 in the paper-based micro-concentrator 500 shown in FIG. 3 is set on a movable bracket. The external electric field 560 includes a cathode 561 and an anode 562. The cathode 561 and the anode 562 can be platinum electrodes, but the present disclosure is not limited thereto. Please refer to FIG. 4 again, the cathode 561 and the anode 562 can be freely moved among the four pairs of the fluid reservoir units 550 by the movable bracket, and the cathode 561 can be placed in the first buffer solution tank 551, and the anode 562 can be placed in the second buffer solution tank 552 to apply the electric field to the paper-based micro-concentrator 500. When one of the filter papers 520 completes the concentration experiment, the external electric field 560 can be moved to the next pair of the fluid reservoir units 550 for another concentration experiment, which increases the convenience of the experiment.

The number of the cation exchange membranes 530 in the paper-based micro-concentrator 500 shown in FIG. 3 is 4, each of the cation exchange membrane 530 is disposed on the filter paper 520 and is close to the first buffer solution tank 551, and the cation exchange membrane 530 is attached to the filter paper 520, the size of the cation exchange membrane 130 can be 6 mm in length and 3 mm in width.

The magnet 540 in the paper-based micro-concentrator 500 is movably disposed under the bearing substrate 510, and the magnet 540 which can be movable can be rotated into or out of a place under the paper-based micro-concentrator 500 according to the requirements of the experiment.

In addition, according to the needs of the experiment, two above-mentioned paper-based micro-concentrators 500 can be fabricated, and the two paper-based micro-concentrators 500 can be connected in series. Because the paper-based micro-concentrator 500 can be put into a plurality of the filter papers 520, it is convenient to perform multi-concentration repeatable experimental detection in the experiment.

II. A BIOLOGICAL SAMPLE DETECTION DEVICE OF THE PRESENT DISCLOSURE

Figure 5:
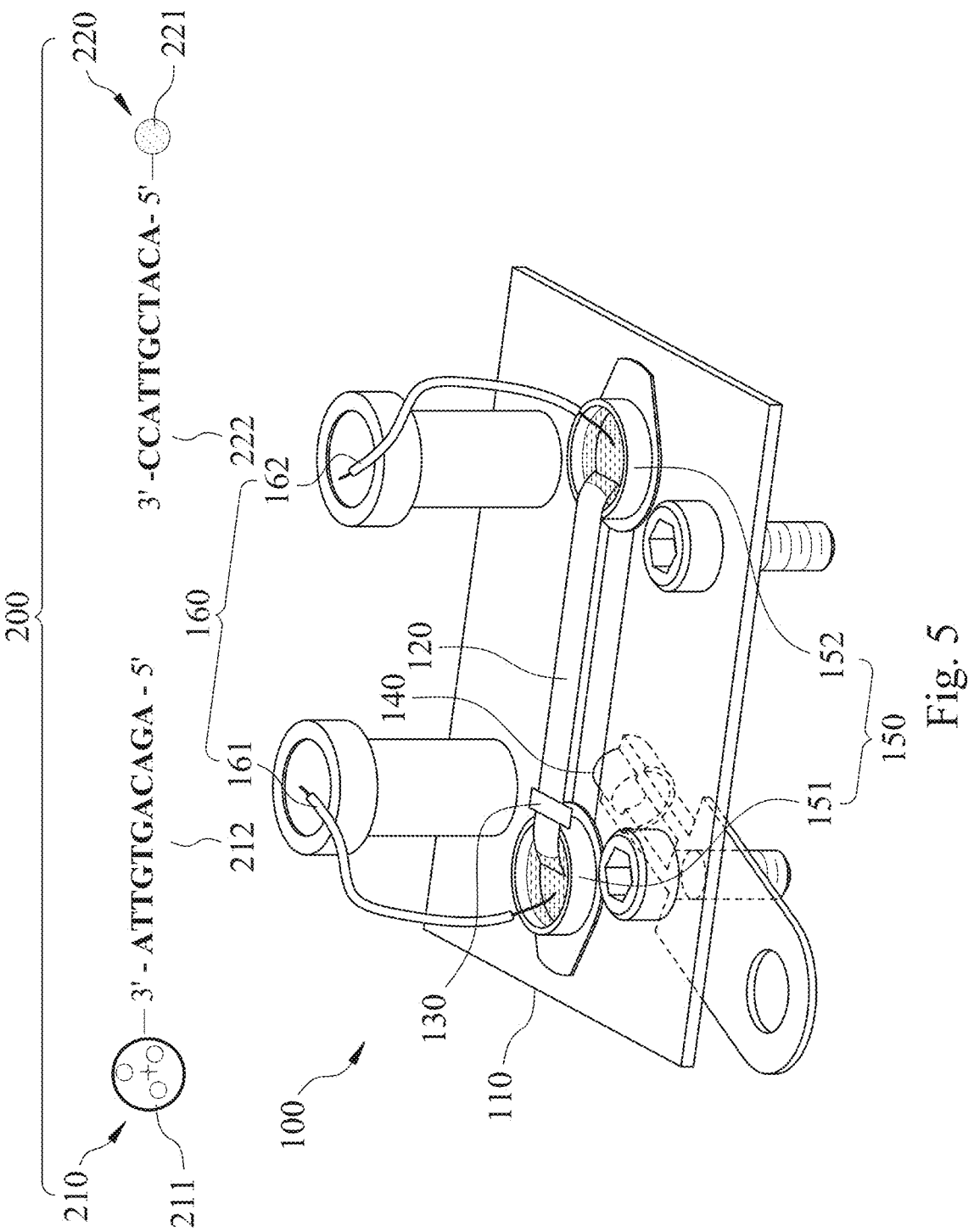
FIG. 5 is a schematic view of a biological sample detection device according to another embodiment of the present disclosure.
Figure 6A:
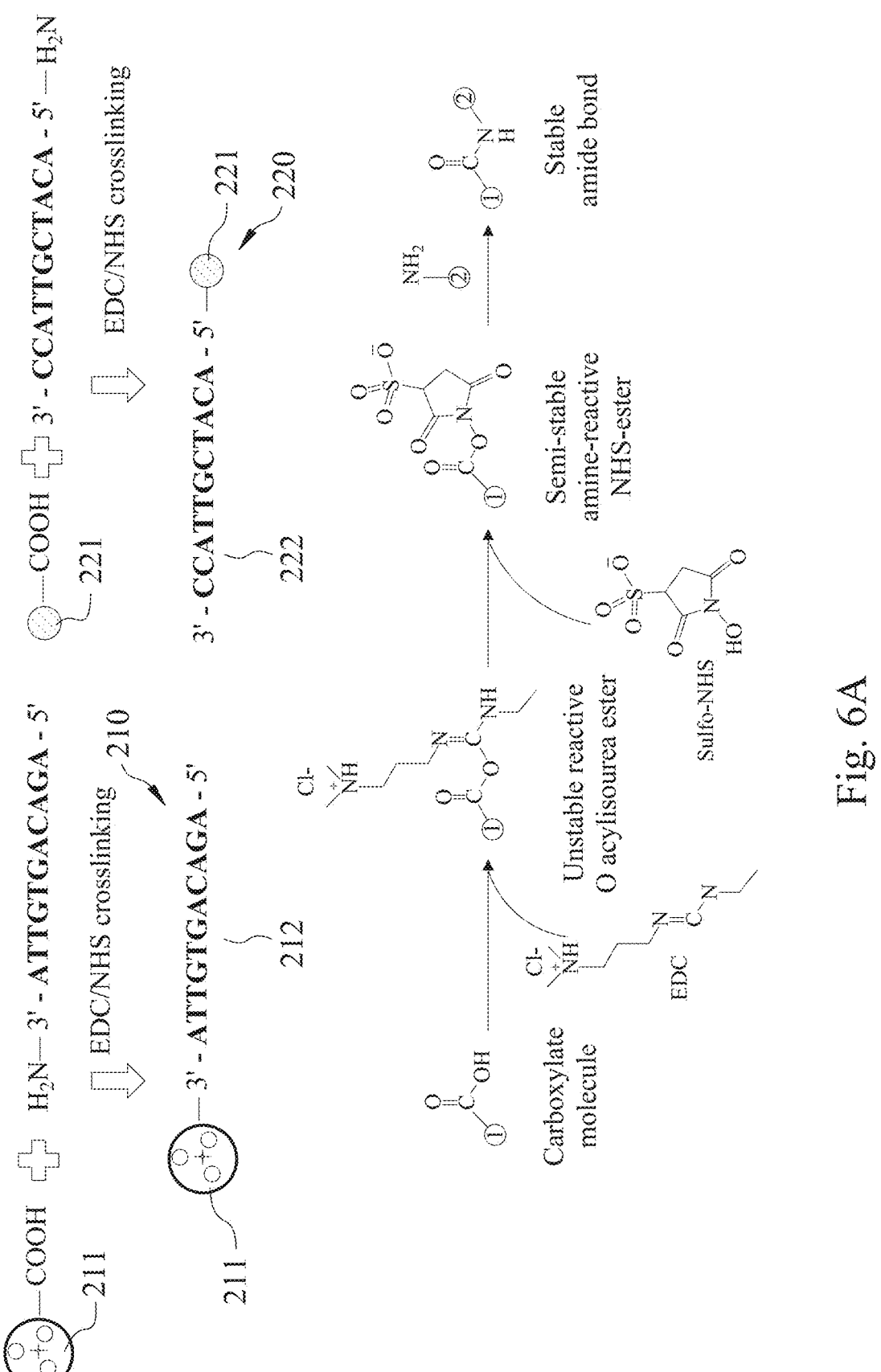
FIG. 6A is a schematic view showing synthesis of a probe set of a biological sample detection device according to one example of another embodiment of the present disclosure.
Figure 6B:
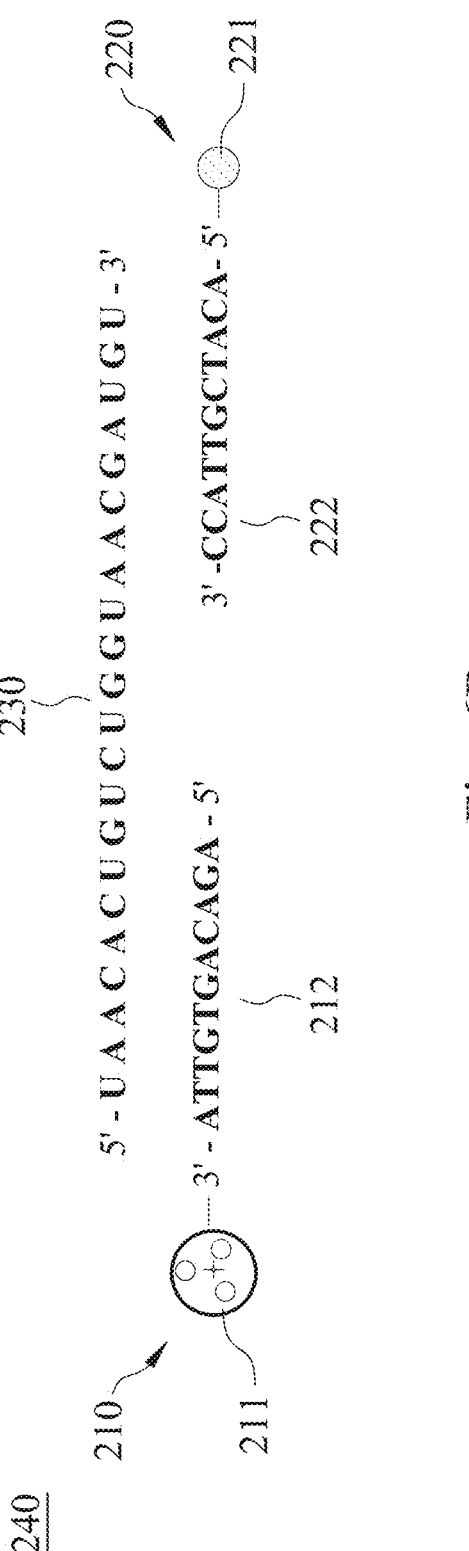
FIG. 6B is a schematic view showing that the probe set shown in FIG. 6A specifically binds to an analyte as a complex.

Please refer to FIG. 5, FIG. 6A and FIG. 6B. FIG. 5 is a schematic view of a biological sample detection device 300 according to another embodiment of the present disclosure. FIG. 6A is a schematic view showing synthesis of a probe set 200 of a biological sample detection device 300 according to one example of another embodiment of the present disclosure. FIG. 6B is a schematic view showing that the probe set 200 shown in FIG. 6A specifically binds to an analyte 230 as a complex 240.

The biological sample detection device 300 is for detecting the analyte 230 in a biological sample. In FIG. 5, the biological sample detection device 300 includes the paper-based micro-concentrator 100 and the probe set 200, wherein the structure of the paper-based micro-concentrator 100 is the same as that of the paper-based micro-concentrator 100 shown in FIG. 1, will not be repeated herein. However, it should be noted that the paper-based micro-concentrator in the biological sample detection device 300 can also be replaced with the paper-based micro-concentrator 100a including the anion exchange membrane 130a according to different samples to be analyzed.

The probe set 200 includes a detection probe 210 and a capture probe 220. The detection probe 210 includes a label 211 and a first identifying element 212, and the capture probe 220 includes a magnetic nanoparticle 221 and a second identifying element 222. The first identifying element 212 and the second identifying element 222 are different, and the first identifying element 212 and the second identifying element 222 specifically bind to the analyte 230, respectively.

The label 211 is a substance that can be covalently bound to the first identifying element 212 or physically adsorbed on the first identifying element 212 and can be used to detect the presence of the complex 240. The label 211 can be a Raman label, a fluorescent label, a chemiluminescence label, a radioisotope label, an enzyme label or a biotin label. Further, the fluorescent label includes, but is not limited to, fluorescent group such as FAM, JOE or VIC. The chemiluminescent label includes, but is not limited to, an electro-chemiluminescent compound or a chemiluminescent compound such as luminol, isoluminol, or acridinium salts. The radioisotope label includes, but is not limited to, $^{3}$H, $^{14}$C, $^{35}$P, $^{35}$S, $^{125(131)}$I, $^{75}$Se. The enzyme label includes, but is not limited to, an enzyme with detectable product such as luciferase, peroxidase, alkaline phosphatase, β-galactosidase, and an analog thereof.

The magnetic nanoparticle 221 can be composed of iron oxide, such as magnetite ($Fe_3O_4$) and maghemite ($Fe_2O_3$). Preferably, a nanoparticle of ferric tetroxide is used as a base material and is reacted with a carboxyl functional group (—COOH) to form the magnetic nanoparticle 221 with the carboxyl group (—COOH) on the surface thereof, which can be bound to a bioprobe with amine end (—NH$_2$) in a biochemically modified manner. Thereby, the magnetic nanoparticle 221 has magnetic properties and high biocompatibility to increase the application range. In addition, an average diameter of the magnetic nanoparticle 221 can be 6 nm to 10 nm. When the average diameter of the magnetic nanoparticle 221 is less than 20 nm, the magnetic nanoparticle 221 has superparamagnetism.

In addition, the magnet 140 in the biological sample detection device 300 is movably disposed under the bearing substrate 110, whereby the magnet 140 can be rotated into the biological sample detection device 300 or rotated out of the biological sample detection device 300 according to the requirements of the experiment. When an electric field is applied to the biological sample detection device 300, the complex 240 including the magnetic nanoparticle 221 will be concentrated close to the cation exchange membrane 130. At this time, the magnet 140 which can be movable can be rotated into the biological sample detection device 300, and the complex 240 can be collected and washed preliminarily by the attractive force of the magnet 140.

Furthermore, when the analyte 230 is a ribonucleic acid, the first identifying element 212 and the second identifying element 222 can be respectively a nucleic acid fragment complementary to the 5' end sequence of the ribonucleic acid and a nucleic acid fragment complementary to the 3' end sequence of the ribonucleic acid. Preferably, the ribonucleic acid can be a microRNA (miRNA). When the analyte 230 is an antigen, the first identifying element 212 and the second identifying element 222 can be respectively an antibody or an aptamer with binding specificity to the antigen, and antigen-binding sites of the first identifying element 212 and the second identifying element 222 with the antigen are different. When the analyte 230 is an antibody, the first identifying element 212 and the second identifying element 222 can be respectively an antigen with binding specificity to the antibody, and antigen-binding sites of the first identifying element 212 and the second identifying element 222 with the antibody are different.

Please refer to FIGS. 6A and 6B again, which is one example of the probe set 200 of the present disclosure. Abnormal expression of miR-200a-3p can be found in ovarian cancer tissues and cells of ovarian cancer patient. However, a concentration of miRNA sample from the ovarian cancer patient is very low, so it is difficult to detect the abnormal expression of miR-200a-3p at an early stage. Therefore, in the test example of the present disclosure, miR-200a-3p is used as the analyte 230, and the sequence of miR-200a-3p is referenced as SEQ ID NO: 1 to verify the detection sensitivity of the biological sample detection device 300 of the present disclosure. Raman label is used as the label 211, and two locked nucleic acid probes (LNA-Probe) complementary to miR-200a-3p are designed as the first identifying element 212 and the second identifying element 222. The first identifying element 212 with the nucleic acid sequence referenced as SEQ ID NO: 2 is complementary to the sequence of the 5' end of miR-200a-3p, and a dissociation constant (Kd) of the first identifying element 212 is about $10^{-9}$M. The second identifying element 222 with the nucleic acid sequence referenced as SEQ ID NO: 3 is complementary to the sequence of the 3' end of miR-200a-3p, and a dissociation constant (Kd) of the second identifying element 222 is about $4.2825 \times 10^{-7}$ M.

In FIG. 6A and FIG. 6B, the label 211 (Raman label) has a carboxyl (—COOH) modified functional group on the surface thereof, and the magnetic nanoparticle 221 also has a carboxyl (—COOH) modified functional group on the surface thereof. The label 211 is bound to the first identifying element 212 with a modified amine end (—NH$_2$) in one end thereof to form the detection probe 210, and the magnetic nanoparticle 221 is bound to the second identifying element 222 with a modified amine end (—NH$_2$) in one end thereof to form the capture probe 220. Then, the detection probe 210, the capture probe 220 and the analyte 230 are conjugated to form the complex 240 by means of base pair complementation through a hybridization reaction. The complex 240, which is bound with the magnetic nanoparticle 221, is dropped onto the paper-based micro-concentrator 100, and after applying a voltage for concentration, the magnet 140 in the paper-based micro-concentrator 100 can attract the complex 240 with the magnetic nanoparticle 221 as a collection method and wash with a buffer to improve the detection sensitivity of miR-200a-3p in the sample, and then detected by the Raman spectrometer to obtain a Raman signal of saffron.

III. A BIOLOGICAL SAMPLE DETECTION METHOD OF THE PRESENT DISCLOSURE

Figure 7:
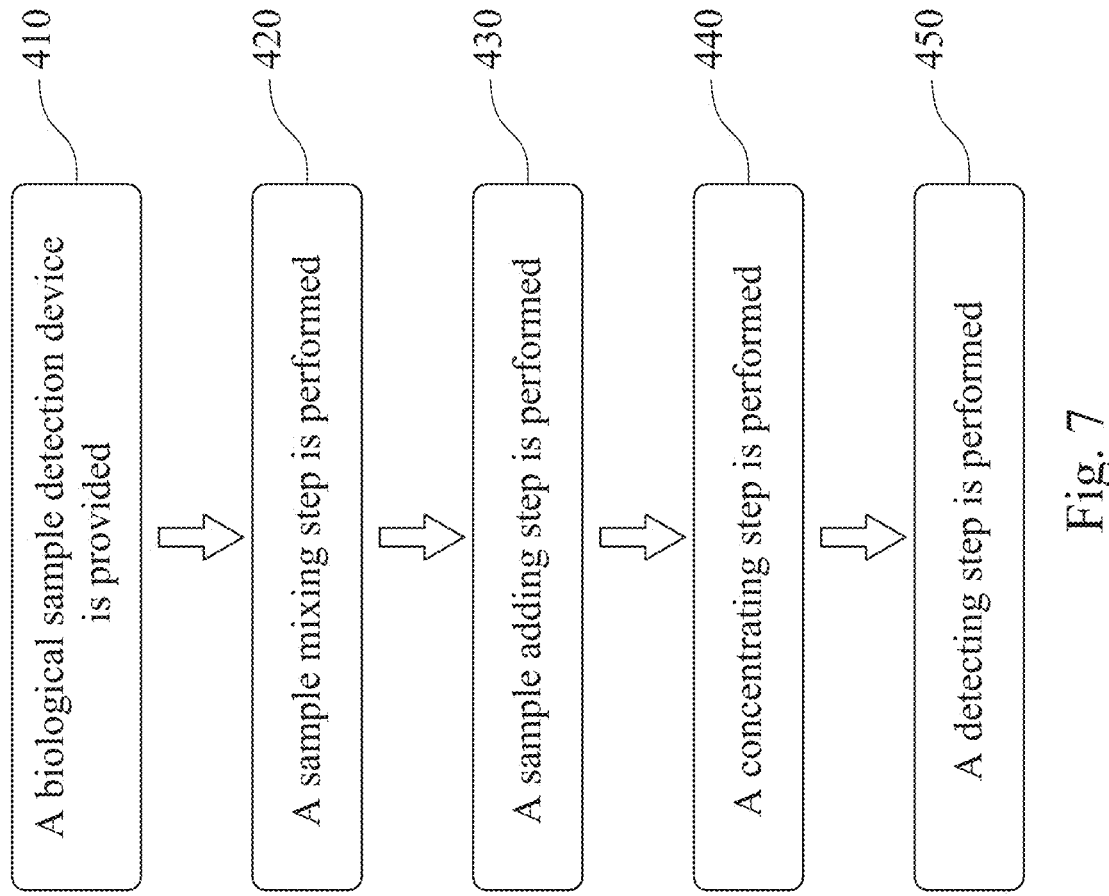
FIG. 7 is a flow diagram showing a biological sample detection method according to still another embodiment of the present disclosure.

Please refer to FIG. 7, which is a flow diagram showing a biological sample detection method 400 according to still another embodiment of the present disclosure. The biological sample detection method 400 of the present disclosure includes a Step 410, a Step 420, a Step 430, a Step 440, and a Step 450.

In the Step 410, a biological sample detection device is provided. In detail, the biological sample detection device 300 of the present disclosure is used in the biological sample detection method 400 of the present disclosure to detect the biological sample, and the structural details of the biological sample detection device 300 of the present disclosure can be found in the previous paragraphs, and will not be repeated herein. However, it should be noted that the biological sample detection device provided in the Step 410 can also be replaced with the paper-based micro-concentrator 100a including the anion exchange membrane 130a according to different samples to be analyzed.

In the Step 420, a sample mixing step is performed. The probe set 200 is mixed with a biological sample, and the detection probe 210 and the capture probe 220 in the probe set 200 are respectively bound to the analyte 230 in the biological sample to form the complex 240.

In the Step 430, a sample adding step is performed. The biological sample including the complex 240 is dropped onto the filter paper 120 of the paper-based micro-concentrator 100.

In the Step 440, a concentrating step is performed. The voltage is applied to the paper-based micro-concentrator 100 for a concentration time to form the concentrating area. The concentration time can be greater than 10 seconds. In addition, the concentrating step can further include rotating the magnet 140 into the concentrating area to attract the complex 240 for a preliminary collection.

In the Step 450, a detecting step is performed. The concentrating area is detected with a detection instrument to detect the concentration of the analyte 230. The detection instrument can be adjusted according to the label 211 in the detection probe 210. For example, when the label 211 of the detection probe 210 is the Raman label, the Raman spectrometer can be used for detection in the detection step.

In addition, the biological sample detection method 400 can further include an ion exchange membrane activating step before the sample mixing step. The ion exchange membrane in this embodiment is the cation exchange membrane 130. The cation exchange membrane 130 can be a RALEX® membrane CMHPES produced by MEGA Corporation, which is made of polyester fiber as the base material and uses polyethylene as the basic binder, and the negatively charged group therein is sulfonate (SO$_3$-). The cation exchange membrane 130 needs to be pretreated by swelling before use. The swelling is to soak the cation exchange membrane 130 in a solvent, and the mechanical, physical and electrochemical properties of the cation exchange membrane 130 will be changed during the swelling process. After the swelling process is completed, the cation exchange membrane 130 will have ionic conductivity. During the swelling process, it is necessary to ensure that the cation exchange membrane 130 is completely immersed in the solvent, so as to remove air bubbles on the surface of the cation exchange membrane 130. In detail, the cation exchange membrane 130 can be activated by using three solvents of 1 M NaOH, 1 M HCl and DI water, and activated by soaking. The activation adjustment parameters are based on different soaking time durations and soaking times, wherein the soaking time durations are 10 minutes, 30 minutes, 10 minutes, 60 minutes, and 1440 minutes, respectively, and the soaking times are 7 times and 11 times, respectively. Furthermore, three solvents of 1 M H$_2$SO$_4$, 1 M NaOH and DI water can also be used, and the cation exchange membrane 130 can be activated by soaking. First, the cation exchange membrane 130 is rinsed with DI water for preliminary washing. After washing, the cation exchange membrane 130 is soaked in DI water for 24 hours, soaked in 1 M $H_2SO_4$ for another 24 hours, washed with DI water, and then soaked in 1 M NaOH for still another 24 hours, and finally stored in DI water. It should be noted that, the activating step of the ion exchange membrane can be adjusted when the ion exchange membrane used is the anion exchange membrane 130a.

In addition, before the detecting step, the biological sample detection method 400 can further include a washing step. In the washing step, the concentrating area is washed with the buffer solution to remove the detection probes that are not bound to the analyte. Preferably, the number of times of washing in the washing step can be 1 time.

IV. EXAMPLES

To confirm whether the paper-based micro-concentrator of the present disclosure can concentrate sample, and whether the biological sample detection device of the present disclosure can be used to detect the biological sample, the ion exchange membrane and the filter paper used in the paper-based micro-concentrator and biological sample detection device in the following tests are the cation exchange membrane and the filter paper with the negatively charged functional group on the surface thereof as examples to verify the test results. However, it should be noted that the ion exchange membrane and filter paper in the paper-based micro-concentrator and biological sample detection device can be replaced by the anion exchange membrane and the filter paper with positively charged functional group on the surface thereof according to the sample to be analyzed.

1. Concentration Effect Test of the Paper-Based Micro-Concentrator of the Present Disclosure In the experiment, a fluorescein with negative charge and a fluorescent particle with negative charge are concentrated using the paper-based micro-concentrator 100 shown in FIG. 1. The fluorescein (Fluorescein sodium salt) used in the experiment is prepared at the concentration of 50 μM in Tris buffer (10 mM). A particle size of the fluorescent particle (Fluoresbrite® YG Microspheres) used in the experiment is about 100 nm. The main component of the fluorescent particle is polystyrene with the concentration of $4.55 \times 10^{13}$ particles/mL, and its excitation and emission spectra are very similar to the fluorescein. The fluorescent particle has a small amount of negative charge, so it is beneficial to use the paper-based micro-concentrator 100 to apply the electric field to generate the ion concentration polarization, thereby indicating that the paper-based micro-concentrator of the present disclosure can concentrate the sample.

Figure 8A:
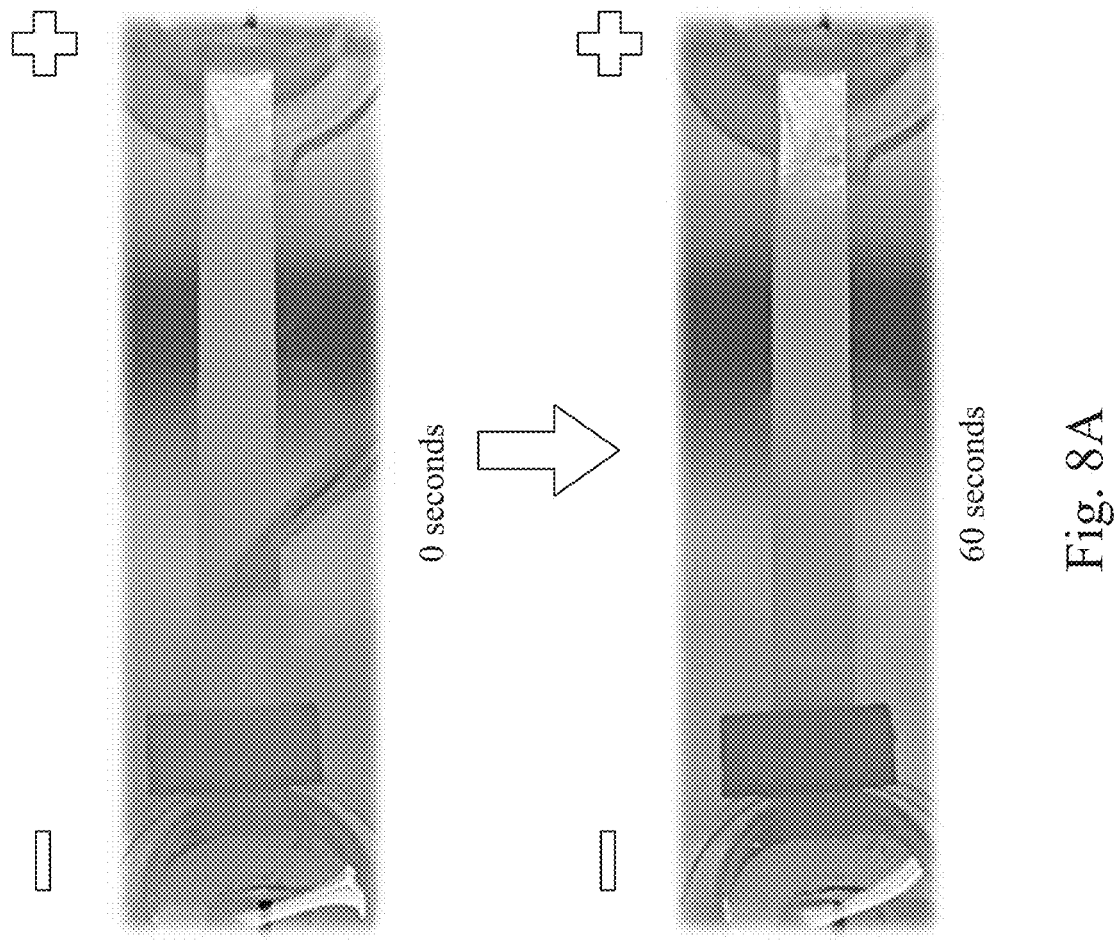
FIG. 8A shows an analytical result of concentrating fluorescein in a paper-based micro-concentrator of the present disclosure.

Please refer to FIG. 8A, which shows an analytical result of concentrating the fluorescein in the paper-based micro-concentrator 100 of the present disclosure. The paper-based micro-concentrator 100 is fabricated in the aforementioned manner, 0.5 μL of the sample drawn and dropped onto the filter paper 120 by using a micropipette. In order to facilitate the observation of the experimental results, a blue LED light is used to illuminate, and the fluorescein will emit green fluorescence when it is illuminated. Tris buffer (10 mM) is used as the buffer solution. Then the paper-based micro-concentrator 100 is applied the electric field with the voltage of 80 V/cm to the cathode 161 and the anode 162. The cation exchange membrane 130 only allows cations to pass through, resulting in the formation of the ion depletion zone in the area of the cation exchange membrane 130 close to the anode 162. At this time, the electroosmotic flow will drive the fluorescein from the anode 162 to the cathode 161, resulting in the accumulation of a plurality of the fluorescein at the edge of the ion depletion zone to form the concentrating area. When the voltage is applied for 60 seconds, the concentrating area of the fluorescein can be clearly observed, and the result indicates that the paper-based micro-concentrator 100 of the present disclosure can concentrate the fluorescein with negative charge.

Figure 8B:
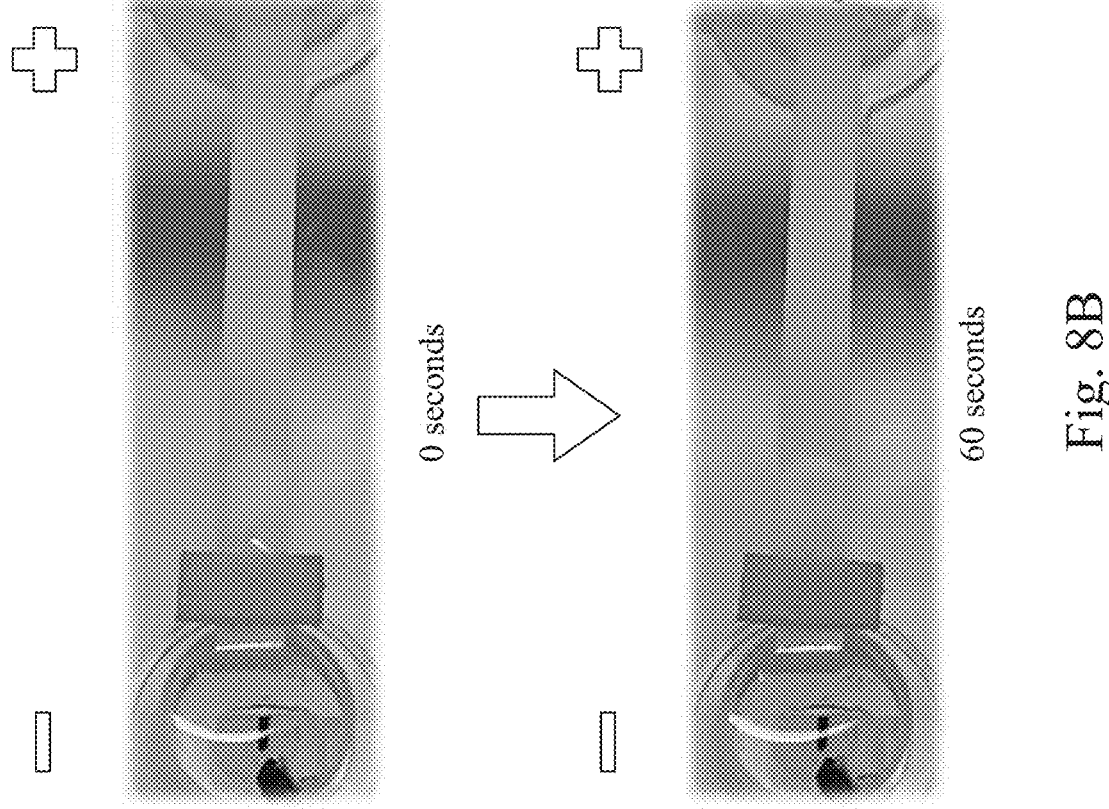
FIG. 8B shows an analytical result of concentrating fluorescent particles in a paper-based micro-concentrator of the present disclosure.

Please refer to FIG. 8B, which shows an analytical result of concentrating the fluorescent particles in the paper-based micro-concentrator 100 of the present disclosure. Because the size of the complex 240 is about 100 nm in the subsequent experiments, the fluorescent particle of about 100 nm is selected as the simulated sample for the experiment. In order to facilitate the observation of the experimental results, the blue LED light is also used in the experiment. When the fluorescent particle is illuminated with blue light, it will emit green fluorescence. The fluorescent particle has a small amount of negative charge, which is beneficial to the ion concentration polarization. Tris buffer (10 mM) is also used as the buffer solution. Then the paper-based micro-concentrator 100 is applied the electric field with the voltage of 80 V/cm. When the voltage is applied for 60 seconds, the concentrating area of the fluorescent particle can be clearly observed, and the result indicates that the paper-based micro-concentrator 100 of the present disclosure can concentrate the analyte with the particle size of about 100 nm and negative charge.

2. Washing Condition Test of the Biological Sample Detection Device of the Present Disclosure for Detection of the Biological Sample The aforementioned experiments have confirmed that the paper-based micro-concentrator 100 of the present disclosure can concentrate the analyte with negative charge. In order to improve the sensitivity of the biological sample detection device of the present disclosure for detecting biological samples, a washing condition test is performed first to test the optimal washing condition for removing the detection probes that are not conjugated to the analyte, so as to reduce signal interference during subsequent detection.

The probe set 200 used in the experiment is shown in FIG. 6A and FIG. 6B as an example, and the analyte 230 (miRNA-200a-3p) is diluted with diethylpyrocarbonate (DEPC) treated water to the concentration of $10^{-16}$ M, and using the micropipette to take 50 μL therefrom into an Eppendorf® tube. Then 25 μL of the detection probe 210 (including the first identifying element 212 referenced as SEQ ID NO: 2), 25 μL of the capture probe 220 (including the second identifying element 222 referenced as SEQ ID NO: 3) and 400 μL of Tris buffer (10 mM) are added into the Eppendorf® tube. The Eppendorf® tube is shaken with a vortex mixer for 60 minutes, and the complex 240 is formed by the hybridization reaction. Then the magnet 140 is used for magnetic attraction for 30 minutes as the preliminary collection. After the magnetic attraction is completed, the supernatant is removed for removing the unconjugated detection probe 210 to reduce the signal interference in the Raman spectrum. The precipitate is redissolved with 10 μL of Tris buffer (10 mM), and the liquid containing the complex 240 is pipetted into the paper-based micro-concentrator 100 using the micropipette.

In addition, in order to confirm whether there is signal interference caused by non-specific adsorption between the detection probe 210 and the capture probe 220, 25 μL of the detection probe 210, 25 μL of the capture probe 220 and 450 μL of Tris buffer (10 mM) are added into an Eppendorf® tube as a blank. The Eppendorf® tube is shaken with the vortex mixer for 60 minutes, and the magnet 140 is used for magnetic attraction for 30 minutes as the preliminary collection. After the magnetic attraction is completed, the supernatant is removed for removing the unconjugated detection probe 210 to reduce the signal interference in the Raman spectrum. The precipitate is redissolved with 10 μL of Tris buffer (10 mM), and the liquid containing the complex 240 is pipetted into the paper-based micro-concentrator 100 using the micropipette.

Figure 9:
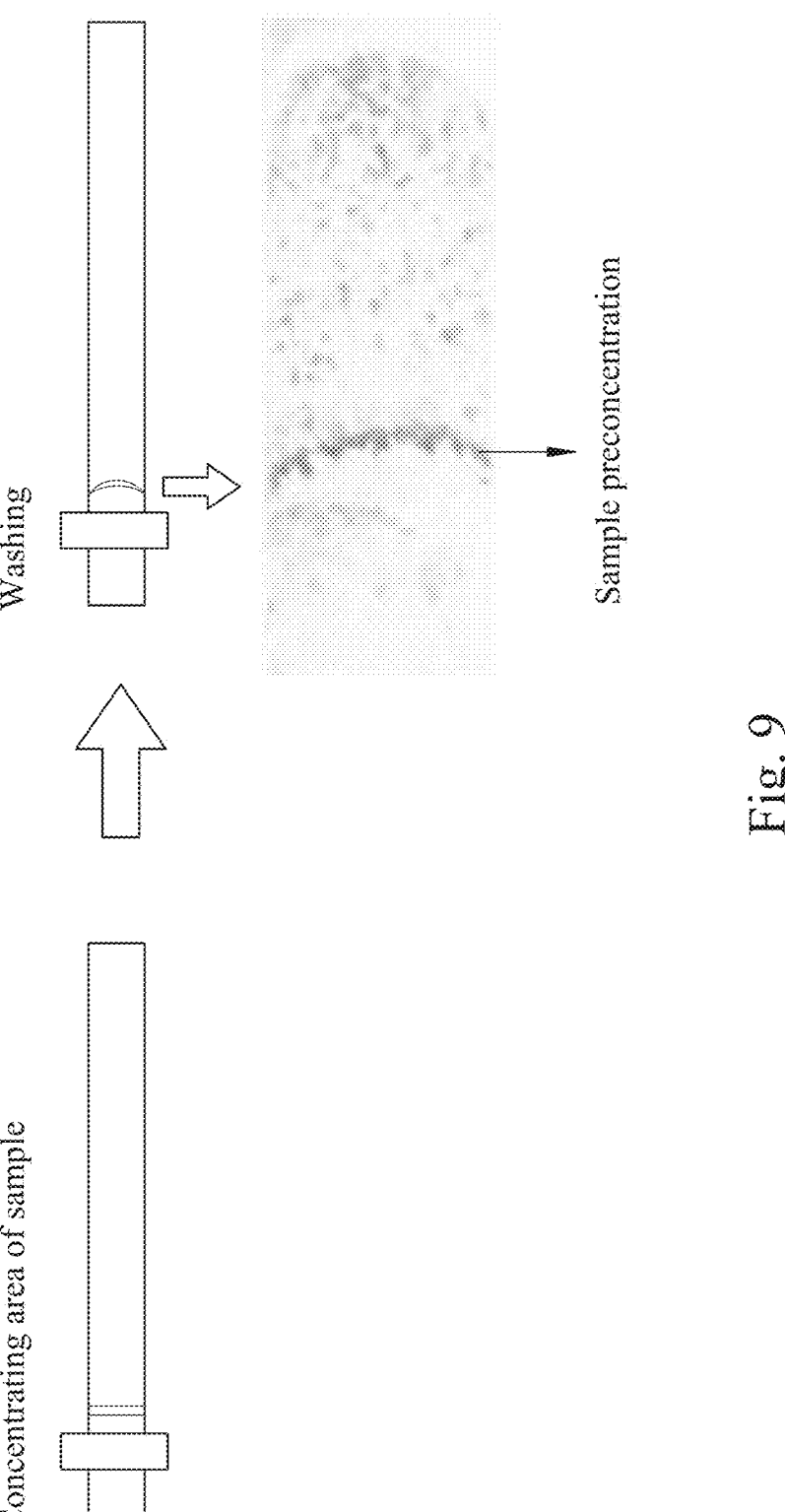
FIG. 9 is a schematic view showing an operation of the biological sample detection device of the present disclosure.

Please refer to FIG. 9, which is a schematic view showing an operation of the biological sample detection device 300 of the present disclosure. The complex 240 including miRNA-200a-3p at the concentration of $10^{-16}$ M and the blank are concentrated using the paper-based micro-concentrator 100. Tris buffer (10 mM) is used as the buffer solution, and the voltage of 80 V/cm is applied to the paper-based micro-concentrator 100. The cation exchange membrane 130 only allows cations to pass through, resulting in the formation of the ion depletion zone in the area of the cation exchange membrane 130 close to the anode 162. At this time, the electroosmotic flow will drive the complex 240 from the anode 162 to the cathode 161, resulting in the accumulation of a plurality of the complexes 240 at the edge of the ion depletion zone to form the concentrating area after being concentrated for 1 minute. The magnet 140 which can be movable designed in the paper-based micro-concentrator 100 is rotated into to attract the complexes 240. Then 10 μL of Tris buffer (10 mM) is drawn by the micropipette to wash the concentrating area of the sample for removing the unconjugated detection probe 210 to reduce the signal interference in the Raman spectrum. After washing, the sample is detected by the Raman spectrometer.

3. Detection Sensitivity of the Biological Sample Detection Device of the Present Disclosure for Detecting the Biological Sample The detection sensitivity of the biological sample detection device of the present disclosure for detecting biological samples is further tested, wherein the biological sample detection device 300 including the paper-based micro-concentrator 100 in FIG. 1 is used subsequent experiments.

The analyte 230 (miRNA-200a-3p) is diluted in DEPC treated water to the concentrations of $10^{-9}$ M, $10^{-10}$ M, $10^{-11}$ M, $10^{-12}$ M, $10^{-13}$ M, $10^{-14}$ M, $10^{-15}$ M, $10^{-16}$ M for establishing a calibration line, and using the micropipette to take 50 μL therefrom into an Eppendorf® tube. Then 25 μL of the detection probe 210 (including the first identifying element 212 referenced as SEQ ID NO: 2), 25 μL of the capture probe 220 (including the second identifying element 222 referenced as SEQ ID NO: 3) and 400 μL of Tris buffer (10 mM) are added into the Eppendorf® tube. The Eppendorf® tube is shaken with the vortex mixer for 60 minutes, and the complex 240 is formed by the hybridization reaction. Then the magnet 140 is used for magnetic attraction for 30 minutes as the preliminary collection. After the magnetic attraction is completed, the supernatant is removed for removing the unconjugated detection probe 210 to reduce the signal interference in the Raman spectrum. The precipitate is redissolved with 10 μL of Tris buffer (10 mM), and the liquid containing the complex 240 is pipetted into the paper-based micro-concentrator 100 using the micropipette for concentration. Tris buffer (10 mM) is also used as the buffer solution, the buffer solution is dropped into the buffer solution tank, and the voltage of 80 V/cm is applied to the paper-based micro-concentrator 100. After being concentrated for 1 minute, a plurality of the complexes 240 are accumulated at the edge of the ion depletion zone to form the concentrating area. At this time, the magnet 140 which can be movable designed in the paper-based micro-concentrator 100 is rotated into a place to attract the complexes 240. Then 10 μL of Tris buffer (10 mM) is drawn by the micropipette to wash the concentrating area of the sample for removing the detection probe 210 that is not bound to the analyte 230 to reduce the signal interference in the Raman spectrum. After washing, the sample is detected by the Raman spectrometer. The parameters of the Raman spectrometer are set to 10× objective lens, 10% aurora filter, 200 μm slit, 1 s exposure time, 10 integration times, and He—Ne laser wavelength of 633 nm.

Figure 10:
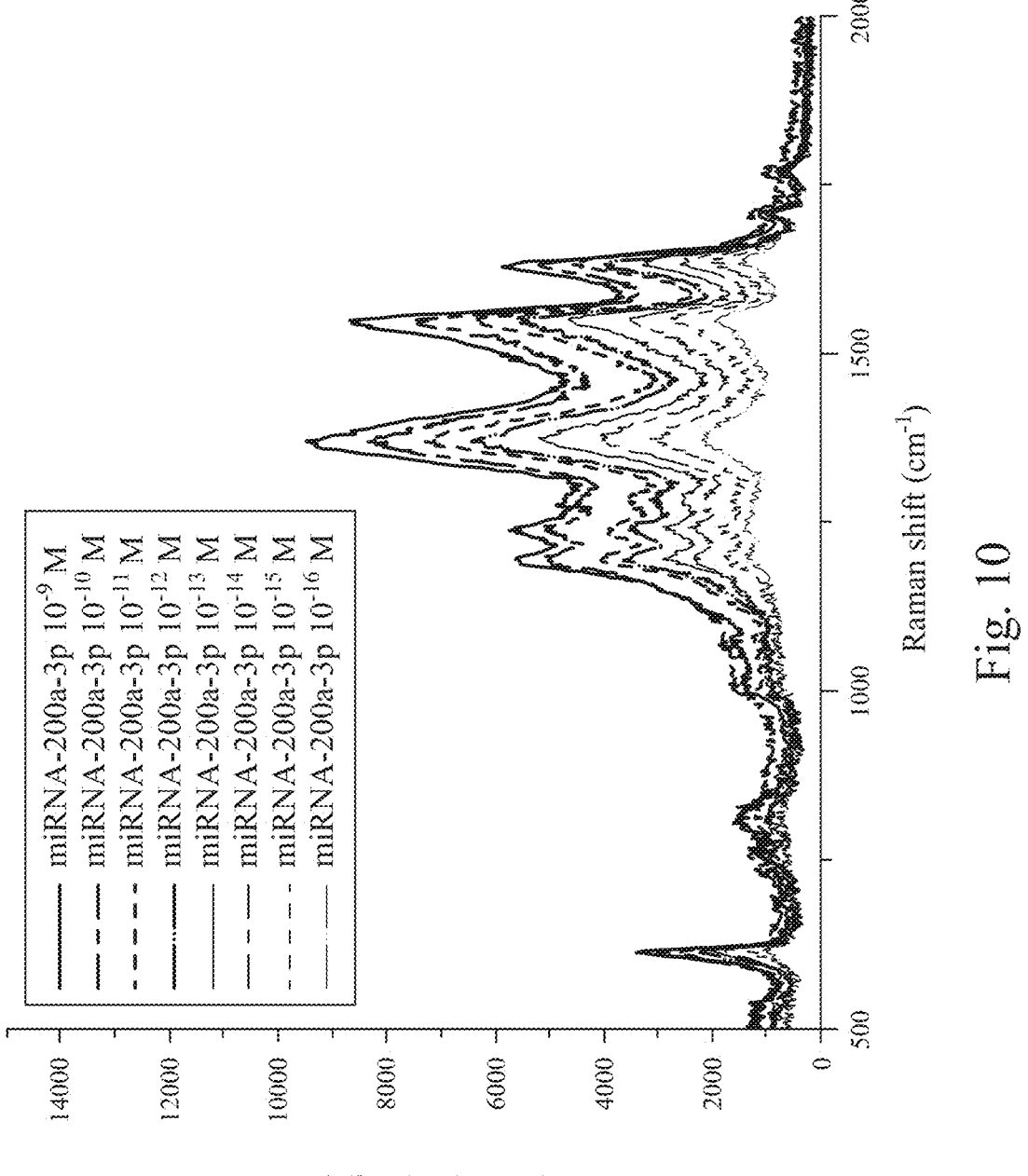
FIG. 10 shows a Raman spectrum of the complexes concentrated using the paper-based micro-concentrator shown in FIG. 1.

Please refer to FIG. 10, which shows a Raman spectrum of the complexes 240 concentrated using the paper-based micro-concentrator 100 shown in FIG. 1. In FIG. 10, the most representative Raman shift of 1378 $cm^{-1}$ is used as a quantitative basis in the Raman spectrum. The intensity of the Raman signal obtained by the Raman spectrometer and a logarithm value of the concentration of the analyte 230 (miRNA-200a-3p) are used for linear regression, and the calibration line for the standard miRNA-200a-3p with a total of eight orders of magnitude from the concentrations of $10^{-9}$ M to $10^{-16}$ M can be obtained. The formula is y=990.44x+ 179930.15, and the $R^2$ value is 0.999. The results indicate that the biological sample detection device of the present disclosure and the biological sample detection method using the same have high selectivity and specificity for miR-200a-3p.

The detection sensitivity of the biological sample detection device 300 including the paper-based micro-concentrator 500 shown in FIG. 3 for detecting biological samples is further tested. miRNA-200a-3p is also selected as the analyte 230, and diluted with DEPC treated water to the concentrations of $10^{-9}$ M, $10^{-10}$ M, $10^{-11}$ M, $10^{-12}$ M, $10^{-13}$ M, $10^{-14}$ M, $10^{-15}$ M, $10^{-16}$ M for establishing a triplicate calibration curve. The experimental conditions are the same as the previous experimental steps, the above experiment is repeated three times, and will not be repeated herein.

Figure 11:
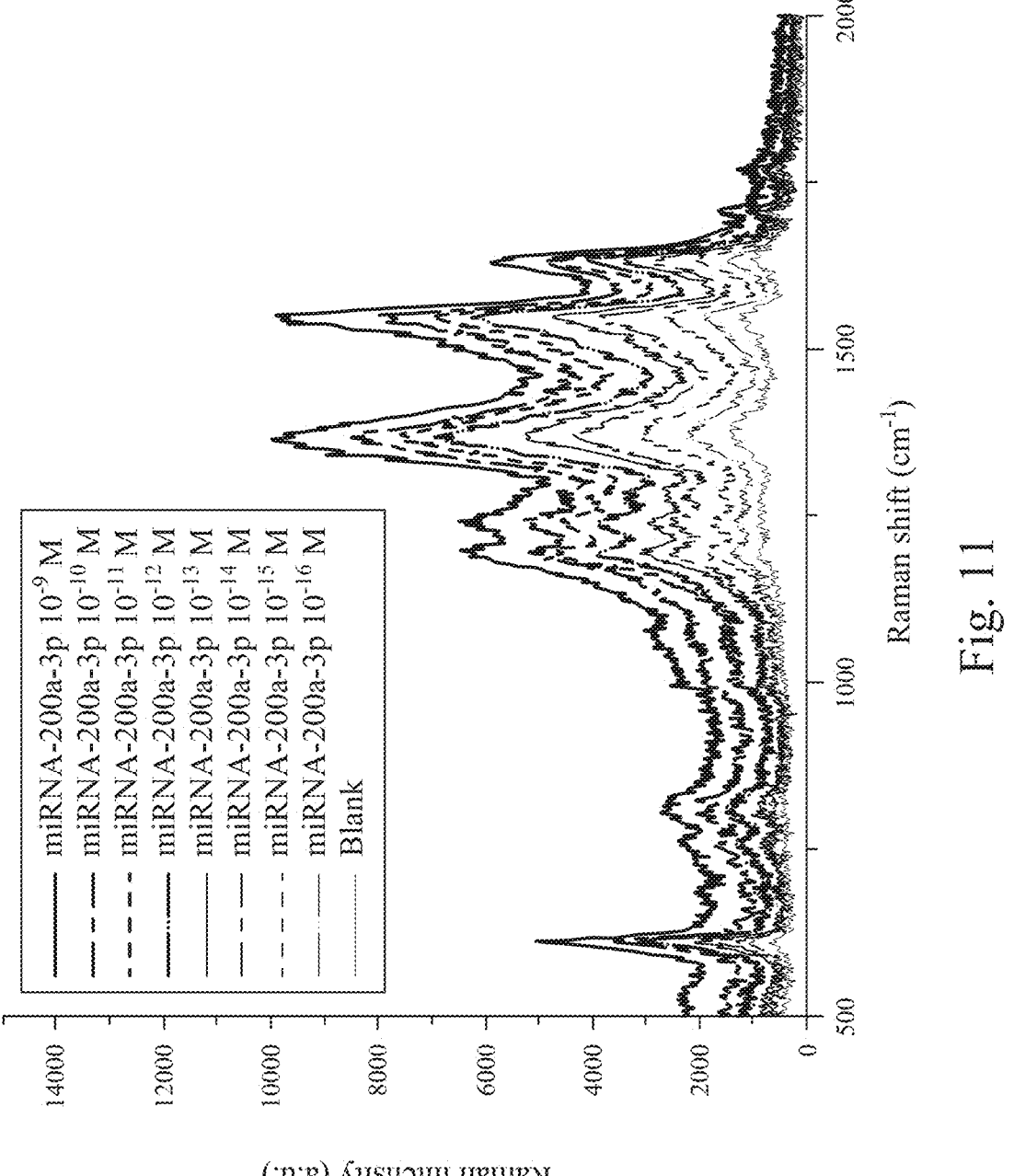
FIG. 11 shows a Raman spectrum of the complexes concentrated using the paper-based micro-concentrator shown in FIG. 3.

Please refer to FIG. 11, which shows a Raman spectrum of the complexes 240 concentrated using the paper-based micro-concentrator 300 shown in FIG. 3. In FIG. 11, the most representative Raman shift of 1378 $cm^{-1}$ is used as the quantitative basis in the Raman spectrum. The intensity of the Raman signal obtained by the Raman spectrometer and the logarithm value of the concentration of the analyte 230 (miRNA-200a-3p) are used for linear regression, and the calibration line for the triplicate standard miRNA-200a-3p with a total of eight orders of magnitude from the concentrations of $10^{-9}$ M to $10^{-16}$ M can be obtained. The formula is y=995.96x+17999.57, and the $R^2$ value is 0.999. The limit of detection (LOD) is calculated by bring the average of three values obtained from the blank plus three times the standard deviation into the calibration line, which represents possible measurement bias due to nonspecific adsorption, and the calculated LOD=$3.57 \times 10^{-17}$ M. The results indicate that the biological sample detection device 300 and the biological sample detection method 400 using the biological sample detection device 300 of the present disclosure have high selectivity and specificity for miR-200a-3p and can further perform multi-concentration repeatability detection.

To sum up, the paper-based micro-concentrator of the present disclosure uses the filter paper as the base material, which makes the manufacturing process very easy, and has the advantages of low price and good portability. The ion exchange membrane is placed on one end of the filter paper and attached to the filter paper. When the external electric field is applied on both sides of the filter paper, in the end of the ion exchange membrane close to the first buffer solution tank and an electrode with the same electrical property as the charged substance, the ion concentration polarization of charged substance will occur. When the cation exchange membrane is used, the ion concentration polarization of negatively charged substance occurs; when the anion exchange membrane is used, the ion concentration polarization of positively charged substance occurs. And the concentrating area is formed in the end of the ion exchange membrane close to the second buffer solution tank and the electrode with opposite electrical polarity as the charged substance, so that the sample can be concentrated.

The biological sample detection device of the present disclosure and the biological sample detection method using the same can complete a series of experimental processes in the biological sample detection device, including dropping the biological sample onto the paper-based micro-concentrator to concentrate, and then performing the next step of detection, which saves time during the experimental operation and reduces the possibility of poor sample recovery. The biological sample is specifically bound to the detection probe and the capture probe to form the complex, and then the biological sample containing the complex is pipetted into the paper-based micro-concentrator of the present disclosure. Through the ion concentration polarization, the complex can be concentrated in the end of the ion exchange membrane close to the second buffer solution tank and the electrode with opposite electrical polarity as the charged substance, so that the concentrating area is formed. In addition, the detection sensitivity of the biological sample can be greatly improved by cooperating the magnetic nanoparticle to assist in the collection of the complex. The detection sensitivity is increased to $3.57 \times 10^{-17}$ M, which has great application potential in the relevant market.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A paper-based micro-concentrator, comprising:
a bearing substrate;
a fluid reservoir unit comprising a first buffer solution tank and a second buffer solution tank, wherein the first buffer solution tank and the second buffer solution tank are interval disposed on the bearing substrate, and the first buffer solution tank and the second buffer solution tank store a buffer solution respectively;
a filter paper disposed on the bearing substrate, wherein two ends of the filter paper are respectively placed in the first buffer solution tank and the second buffer solution tank;
an external electric field comprising a cathode and an anode, wherein the cathode and the anode are respectively placed in the first buffer solution tank and the second buffer solution tank;
an ion exchange membrane disposed on the filter paper and close to the first buffer solution tank; and a magnet movably disposed under the bearing substrate;
wherein the ion exchange membrane is a cation exchange membrane or an anion exchange membrane;
wherein when the ion exchange membrane is the cation exchange membrane, a surface of the filter paper has a negatively charged functional group, the cathode is placed in the first buffer solution tank, and the anode is placed in the second buffer solution tank;
wherein when the ion exchange membrane is the anion exchange membrane, a surface of the filter paper has a positively charged functional group, the anode is placed in the first buffer solution tank, and the cathode is placed in the second buffer solution tank.

2. The paper-based micro-concentrator of claim 1, wherein a minimum dimension of a length, a width and a height of the filter paper is greater than 0 mm and less than or equal to 1 mm.

3. A biological sample detection device for detecting an analyte in a biological sample, the biological sample detection device comprising:

the paper-based micro-concentrator of claim 1; and a probe set, comprising:

a detection probe, comprising a label and a first identifying element; and a capture probe, comprising a magnetic nanoparticle and a second identifying element;

wherein the first identifying element and the second identifying element are different, and the first identifying element and the second identifying element specifically bind to the analyte, respectively.

4. The biological sample detection device of claim 3, wherein the label is a Raman label, a fluorescent label, a chemiluminescence label, a radioisotope label, an enzyme label or biotin label.

5. The biological sample detection device of claim 3, wherein an average diameter of the magnetic nanoparticle ranges from 6 nm to 10 nm.

6. The biological sample detection device of claim 3, wherein when the analyte is a ribonucleic acid, the first identifying element and the second identifying element are respectively a nucleic acid fragment complementary to a 5' end sequence of the ribonucleic acid and a nucleic acid fragment complementary to a 3' end sequence of the ribonucleic acid.

7. The biological sample detection device of claim 6, wherein the ribonucleic acid is a microRNA (miRNA).

8. The biological sample detection device of claim 3, wherein when the analyte is an antigen, the first identifying element and the second identifying element are respectively an antibody or an aptamer with binding specificity to the antigen, and antigen-binding sites of the first identifying element and the second identifying element with the antigen are different.

9. The biological sample detection device of claim 3, wherein when the analyte is an antibody, the first identifying element and the second identifying element are respectively an antigen with binding specificity to the antibody, and antigen-binding sites of the first identifying element and the second identifying element with the antibody are different.

10. A biological sample detection method, comprising:

providing the biological sample detection device of claim 3;

performing a sample mixing step, wherein the probe set is mixed with the biological sample, and the detection probe and the capture probe in the probe set are respectively bound to the analyte in the biological sample to form a complex;

performing a sample adding step, wherein the biological sample comprising the complex is dropped onto the filter paper of the paper-based micro-concentrator;

performing a concentrating step, wherein a voltage is applied to the paper-based micro-concentrator for a concentration time to form a concentrating area; and performing a detecting step, wherein the concentrating area is detected with a detection instrument to detect a concentration of the analyte.

11. The biological sample detection method of claim 10, wherein the concentration time is greater than 10 seconds.

12. The biological sample detection method of claim 10, wherein the concentrating step further comprises rotating the magnet into the concentrating area to attract the complex for a preliminary collection.

13. The biological sample detection method of claim 12, further comprising a washing step before the detecting step, wherein the concentrating area is rinsed with a buffer solution to remove the detection probe that is not bound to the analyte.

* * * * *

SEQUENCE LISTING

```
Sequence total quantity: 3
SEQ ID NO: 1              moltype = RNA   length = 22
FEATURE                  Location/Qualifiers
source                   1..22
                         mol_type = other RNA
                         organism = synthetic construct
SEQUENCE: 1
taacactgtc tggtaacgat gt                                    22

SEQ ID NO: 2              moltype = DNA   length = 11
FEATURE                  Location/Qualifiers
source                   1..11
                         mol_type = other DNA
                         organism = synthetic construct
SEQUENCE: 2
agacagtgtt a                                                11

SEQ ID NO: 3              moltype = DNA   length = 11
FEATURE                  Location/Qualifiers
source                   1..11
                         mol_type = other DNA
                         organism = synthetic construct
SEQUENCE: 3
acatcgttac c                                                11
```